US009089135B2

(12) United States Patent
Andersch et al.

(10) Patent No.: US 9,089,135 B2
(45) Date of Patent: Jul. 28, 2015

(54) NEMATICIDAL, INSECTICIDAL AND ACARICIDAL ACTIVE INGREDIENT COMBINATIONS COMPRISING PYRIDYL-ETHYLBENZAMIDES AND INSECTICIDES

(75) Inventors: Wolfram Andersch, Bergisch Gladbach (DE); Heike Hungenberg, Langenfeld (DE); Heiko Rieck, Burscheid (DE)

(73) Assignee: Bayer Intellectual Property GmbH, Monheim (DE)

( * ) Notice: Subject to any disclaimer, the term of this patent is extended or adjusted under 35 U.S.C. 154(b) by 361 days.

(21) Appl. No.: 12/731,812

(22) Filed: Mar. 25, 2010

(65) Prior Publication Data

US 2010/0249193 A1 Sep. 30, 2010

(30) Foreign Application Priority Data

Mar. 25, 2009 (EP) .................................. 09156175

(51) Int. Cl.
*A01N 25/00* (2006.01)
*A01N 43/40* (2006.01)

(52) U.S. Cl.
CPC ..................................... *A01N 43/40* (2013.01)

(58) Field of Classification Search
CPC ....................................................... C05G 3/02
USPC ......................................................... 424/405
See application file for complete search history.

(56) References Cited

U.S. PATENT DOCUMENTS

| 2,596,076 | A | 5/1952 | Hook et al. |
| 2,978,479 | A | 4/1961 | Kayser et al. |
| 3,112,244 | A | 11/1963 | Goyette et al. |
| 3,217,037 | A | 11/1965 | Payne, Jr. et al. |
| 3,244,586 | A | 4/1966 | Rigterink |
| 3,313,684 | A | 4/1967 | Schegk et al. |
| 3,470,299 | A | 9/1969 | Heiss et al. |
| 3,530,220 | A | 9/1970 | Buchanan et al. |
| 3,867,396 | A | 2/1975 | Dawes et al. |
| 3,962,316 | A | 6/1976 | Kiehs et al. |
| 4,004,031 | A | 1/1977 | Drabek et al. |
| 4,006,231 | A | 2/1977 | Black et al. |
| 4,245,432 | A | 1/1981 | Dannelly et al. |
| 4,272,417 | A | 6/1981 | Barke et al. |
| 4,310,519 | A | 1/1982 | Albers-Schonberg et al. |
| 4,474,775 | A | 10/1984 | Okada et al. |
| 4,782,174 | A | 11/1988 | Fuchs et al. |
| 4,808,430 | A | 2/1989 | Kouno |
| 4,889,872 | A | 12/1989 | Naumann et al. |
| 5,876,739 | A | 3/1999 | Turnblad et al. |
| 6,114,374 | A | 9/2000 | Lieb et al. |
| 6,255,342 | B1 | 7/2001 | Lieb et al. |
| 6,359,151 | B2 | 3/2002 | Lieb et al. |
| 7,247,647 | B2 | 7/2007 | Hughes et al. |
| 7,572,818 | B2 | 8/2009 | Mansfield et al. |
| 2002/0010204 | A1 | 1/2002 | Lieb et al. |
| 2003/0176428 | A1 | 9/2003 | Schneidersmann et al. |
| 2006/0111403 | A1 | 5/2006 | Hughes et al. |
| 2007/0203191 | A1* | 8/2007 | Loso et al. ..................... 514/336 |
| 2009/0247551 | A1 | 10/2009 | Jeschke et al. |
| 2009/0253749 | A1 | 10/2009 | Jeschke et al. |
| 2010/0240705 | A1 | 9/2010 | Jeschke et al. |
| 2011/0110906 | A1 | 5/2011 | Andersch et al. |
| 2014/0005047 | A1 | 1/2014 | Hungenberg el al. |

FOREIGN PATENT DOCUMENTS

| EP | 0 146 748 B1 | 5/1988 |
| EP | 0 160 344 B1 | 6/1988 |
| EP | 0 538 588 A1 | 4/1993 |
| EP | 0 580 374 A1 | 1/1994 |
| WO | WO 83/00870 A1 | 3/1983 |
| WO | WO 97/22593 A1 | 6/1997 |
| WO | WO 02/28186 A2 | 4/2002 |
| WO | WO 02/080675 A1 | 10/2002 |
| WO | WO 03/015519 A1 | 2/2003 |
| WO | WO 2004/016088 A2 | 2/2004 |
| WO | WO 2005/077901 A1 | 8/2005 |
| WO | WO 2007/115646 A1 | 10/2007 |
| WO | WO 2007115644 A1 * | 10/2007 |
| WO | WO 2007/149134 A1 | 12/2007 |
| WO | WO 2008/003738 A1 | 1/2008 |
| WO | WO 2009147205 A2 * | 12/2009 |

OTHER PUBLICATIONS

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

Blackshaw, R.E., "Synergistic Mixes of DPX-A7881 and Clopyralid in Canola (*Brassica napus*)," *Weed Tech.* 3:690-695, The Weed Science Society of America, United States (1989).

Blackshaw, R.E., et al., "Herbicide Combinations for Postemergent Weed Control in Safflower (*Carthamus tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

Bradley, P.R., et al., "Response of *Sorghum* (*Sorghum bicolor*) to Atrazine, Ammonium Sulfate, and Glyphosate," *Weed Tech.* 14:15-18, The Weed Science Society of America, United States (2000).

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

(Continued)

*Primary Examiner* — Benjamin Packard
(74) *Attorney, Agent, or Firm* — Sterne, Kessler, Goldstein & Fox PLLC

(57) ABSTRACT

The present invention relates to novel active ingredient combinations which consist of fluopyram and further known active insecticidal ingredients, and are very suitable for controlling animal pests, such as insects and/or unwanted acarids and/or nematodes, in foliar and soil application and/or in seed treatment.

28 Claims, No Drawings

(56) References Cited

OTHER PUBLICATIONS

Colby, S.R., "Calculating synergistic and antagonistic responses of herbicide Combinations," *Weeds* 15:20-22, Weed Science Society of America, United States (1967).

Flint, J.L., et al., "Analyzing Herbicide Interactions, a Statistical Treatment of Colby's Method," *Weed Tech.* 2:304-309, The Weed Science Society of America, United States (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, N.K., and O'Sullivan, P.A., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain *Sorghum* (*Sorghum bicolor*) and Corn (*Zea mays*)," *Weed Tech.* 10:299-304, The Weed Science Society of America, United States (1996).

Lanclos, D.Y., et al.,"Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E., and Allen, R.L., "Interaction of Graminicides Applied in Combination with Pyrithiobac," *Weed Tech.* 10:889-892, The Weed Science Society of America, United States (1996).

Sun, Y.-P. & Johnson, E.R., "Analysis of Joint Action of Insecticides against House Flies", *J. Econ. Entomol.*, 53:887-892, Journal of Economic Entomology, United States (1960).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

English language abstract of European Patent Publication No. EP 0 538 588 A1 (1993).

Office Action mailed Dec. 8, 2014, in U.S. Appl. No. 13/990,586, Hungenberg, H., et al., § 371(c) Date: Sep. 18, 2013, U.S. Patent and Trademark Office, Alexandria, VA.

\* cited by examiner

NEMATICIDAL, INSECTICIDAL AND ACARICIDAL ACTIVE INGREDIENT COMBINATIONS COMPRISING PYRIDYL-ETHYLBENZAMIDES AND INSECTICIDES

The present invention relates to novel active ingredient combinations which consist of fluopyram and further known active insecticidal ingredients, and are very suitable for controlling animal pests, such as insects and/or unwanted acarids and/or nematodes, in foliar and soil application and/or in seed treatment.

It is already known that particular pyridylethylbenzamides possess fungicidal, insecticidal and acaricidal and nematicidal properties.

WO 2004/016088 describes pyridylethylbenzamides and the use thereof as fungicides. The possibility of a combination of one or more of the pyridylethylbenzamide derivatives disclosed with further known fungicides, insecticides, nematicides or acaricides for broadening the spectrum of activity is likewise described. However, the application teaches neither which insecticidal mixing partners are suitable nor the mixing ratio in which insecticides and pyridylethylbenzamide derivatives are combined with one another. WO 2005/077901 teaches fungicidal compositions comprising at least one pyridylethylbenzamide, a fungicide and an inhibitor of electron transport in the respiratory chain of fungi. However, the patent application does not describe any mixtures of pyridylethylbenzamides with insecticides. WO 2008/003738 teaches fungicidal compositions comprising at least one pyridylethylbenzamide and an insecticide. A possible nematicidal effect of the compositions is described in the application, but not explicitly for mixtures comprising N-{2-[3-chloro-5-(trifluoromethyl)-2-pyridinyl]ethyl}-2-trifluoromethylbenzamide.

The efficacy of the active ingredients and active ingredient compositions described in the prior art is good, but leaves something to be desired at low application rates in some cases, especially in the control of nematodes.

It is therefore an object of the present invention to provide nematicidal, insecticidal and acaricidal active ingredient combinations with improved efficacy, especially towards nematodes.

It has now been found that active ingredient combinations comprising (I) N-{2-[3-chloro-5-(trifluoromethyl)-2-pyridinyl]ethyl}-2-trifluoromethylbenzamide (fluopyram)
and the N-oxides thereof;
and
(II) at least one insecticidal or nematicidal active ingredient selected from the group consisting of aldicarb (II-1), carbofuran (II-2), oxamyl (II-3), carbosulfan (II-4), cloethocarb (II-5), thiodicarb (II-6), fenamiphos (II-7), ethoprophos (II-8), terbufos (II-9), isazofos (II-10), pyraclofos (II-11), cadusafos (II-12), chlorethoxyfos (II-13), fosthiazate (II-14), chlorpyriphos-methyl (II-15), benzisothiazole (II-16), abamectin (II-17), fumigants (II-18), *Pasteuria penetrans* (II-19), *Bacillus firmus* (II-20), *Bacillus firmus* I-1582 (BioNem, Votivo) (II-20a), *Metarhizium* (II-21), mycorrhiza (II-22), *Hirsutella* (II-23), 4-{[(6-bromopyrid-3-yl)methyl](2-fluoroethyl)amino}furan-2(5H)-one (II-24), 4-{[(6-fluoropyrid-3-yl)methyl](2,2-difluoroethyl)amino}furan-2(5H)-one (II-25), 4-{[(2-chloro-1,3-thiazol-5-yl)methyl](2-fluoroethyl)amino}furan-2(5H)-one (II-26), 4-{[(6-chloropyrid-3-yl)methyl](2-fluoroethyl)amino}furan-2(5H)-one (II-27), 4-{[(6-chloropyrid-3-yl)methyl](2,2-difluoroethyl)amino}furan-2(5H)-one (II-28), 4-{[(6-chloro-5-fluoropyrid-3-yl)methyl](methyl)amino}furan-2(5H)-one (II-29), 4-{[(5,6-dichloropyrid-3-yl)methyl](2-fluoroethyl)amino}furan-2(5H)-one (1'-30), 4-{[(6-chloro-5-fluoropyrid-3-yl)methyl](cyclo-propyl)amino}furan-2(5H)-one (II-31), 4-{[(6-chloropyrid-3-yl)methyl] (cyclopropyl)amino}furan-2(5H)-one (II-32), 4-{[(6-chloropyrid-3-yl)methyl](methyl)amino}furan-2(5H)-one (II-33), β-cyfluthrin (II-34), transfluthrin (II-35), cyazypyr (II-36), chlorantraniliprole (II-37), ethiprole (II-38), sulfoxaflor (II-39), flonicamid (II-40), methiocarb (II-41), spirotetramat (II-42) and 5-chloro-2-[(3,4,4-trifluorobut-3-en-1-yl)sulphonyl]-1,3-thiazole (II-43) are very suitable for controlling phytopathogenic fungi and animal pests, especially nematodes, in foliar and soil application, especially in seed treatment.

The insecticides or active nematicidal ingredients of group (II) are selected from the group consisting of:
aldicarb (II-1) known from U.S. Pat. No. 3,217,037
and/or
carbofuran (II-2) known from DE-A-1493646
and/or
oxamyl (II-3) known from DE-A-1768623
and/or
carbosulfan (II-4) known from DE-A-2433680
and/or
cloethocarb (II-5) known from DE-A-2231249
and/or
thiodicarb (II-6) known from DE-A-2530439
and/or
fenamiphos (II-7) known from DE-A-1121882
and/or
ethoprophos (II-8) known from U.S. Pat. No. 3,112,244
and/or
terbufos (II-9) known from U.S. Pat. No. 2,596,076
and/or
isazofos (II-10) known from DE-A-2260015
and/or
pyraclofos (II-11) known from DE-A-3012193
and/or
cadusafos (II-12) known from WO 83/00870
and/or
chlorethoxyfos (II-13) known from EP-A-160344
and/or
fosthiazate (II-14) known from EP-A-146748
and/or
chlorpyriphos-methyl (II-15) known from U.S. Pat. No. 3,244,586
and/or
benzisothiazole (II-16),
and/or
abamectin (II-17) known from DE-A-27 17 040,
fumigants (II-18),
*Pasteuria penetrans* (II-19),
and/or
*Bacillus firmus* (II-20),
and/or
*Bacillus firmus* I-1582 (BioNem, Votivo) (II-20a),
and/or
*Metarhizium* (II-21),
and/or
Mycorrhiza (II-22). Mycorrhiza refer to a class of active ingredients which stimulate the growth of mycorrhizal fungi and as a result improve the active ingredient uptake of plants. These include, for example, the strigolactones of the following formulae (II-22a to II-22k):

(II-22a) 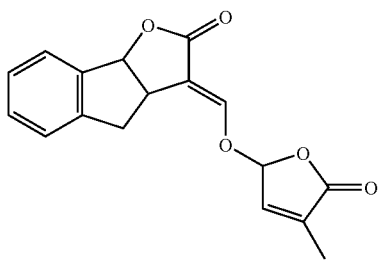

(II-22b) 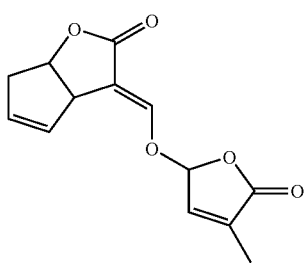

(II-22c) 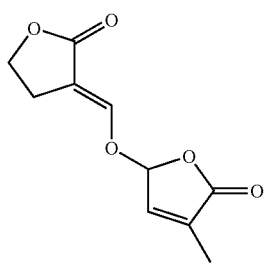

(II-22d) 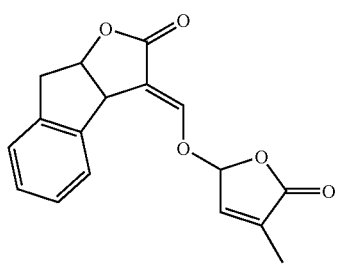

(II-22e) 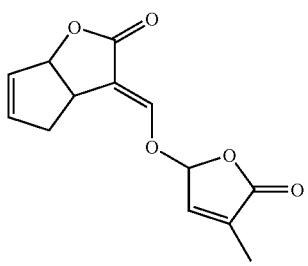

(II-22f) 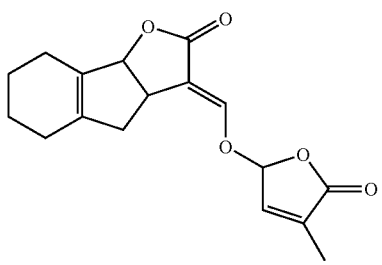

(II-22g) 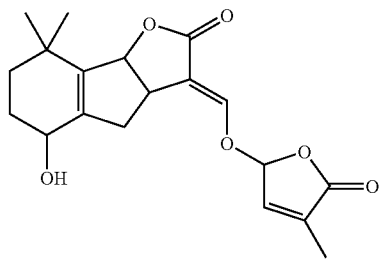

(II-22h) 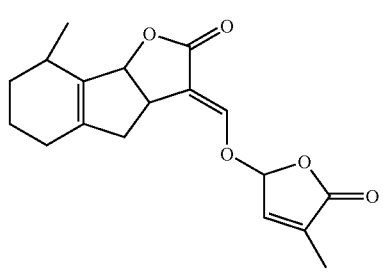

(II-22j) 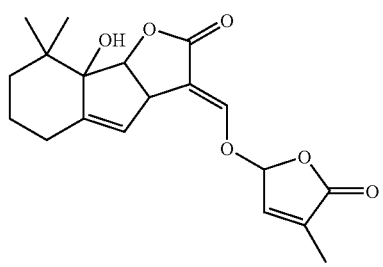

(II-22k) 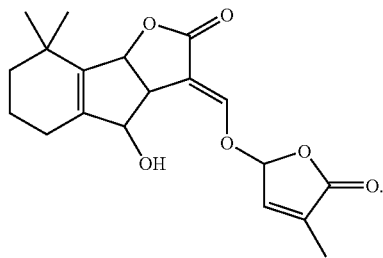

and/or
*Hirsutella* (II-23),
and/or
4-{[(6-bromopyrid-3-yl)methyl](2-fluoroethyl) amino}furan-2(5H)-one (II-24) known from WO 2007/115644 A1,
and/or
4-{[(6-fluoropyrid-3-yl)methyl](2,2-difluoroethyl) amino}furan-2(5H)-one (II-25) known from WO 2007/115644 A1,
and/or
4-{[(2-chloro-1,3-thiazol-5-yl)methyl](2-fluoroethyl) amino}furan-2(5H)-one (II-26) known from WO 2007/115644 A1,
and/or
4-{[(6-chloropyrid-3-yl)methyl](2-fluoroethyl) amino}furan-2(5H)-one (II-27) known from WO 2007/115644 A1,
and/or
4-{[(6-chloropyrid-3-yl)methyl](2,2-difluoroethyl) amino}furan-2(5H)-one (II-28) known from WO 2007/115644 A1,
and/or 4-{[(6-chloro-5-fluoropyrid-3-yl)methyl](methyl) amino}furan-2(5H)-one (II-29) known from WO 2007/115643 A1,
and/or
4-{[(5,6-dichloropyrid-3-yl)methyl}(2-fluoroethyl)amino] furan-2(5H)-one (II-30) known from WO 2007/115646 A1,
and/or
4-{[(6-chloro-5-fluoropyrid-3-yl)methyl](cyclopropyl) amino}furan-2(5H)-one (II-31) known from WO 2007/115643 A1,
and/or
4-{[(6-chloropyrid-3-yl)methyl](cyclopropyl)amino}furan-2(5H)-one (II-32) known from EP 0 538 588 A,
and/or
4-{[(6-chloropyrid-3-yl)methyl](methyl)amino}furan-2 (5H)-one (II-33) known from EP 0 538 588 A,
and/or
β-cyfluthrin (II-34) known from EP-A-206149,
and/or
transfluthrin (II-35) known from EP-A-279325,
and/or
cyazypyr (II-36) known from WO 04/067528,
and/or
chlorantraniliprole (II-37) known from WO 03/015519,
and/or
ethiprole (II-38) known from WO 97/22593,
and/or
sulfoxaflor (II-39) known from WO 2007/149134,
and/or
flonicamid (II-40) known from EP-A-00580374,
and/or
methiocarb (II-41) known from DE-A 11 62 352,
and/or
spirotetramat (II-42) known from WO 98/005638
and/or
5-chloro-2-[(3,4,4-trifluorobut-3-en-1-yl)sulphonyl]-1,3-thiazole (II-43) known from WO 01/02378.

In a preferred embodiment of the invention, the insecticidal or nematicidal active ingredients of group (II) are selected from the group consisting of benzisothiazole (II-16), fumigants (II-18), *Pasteuria penetrans* (II-19), *Bacillus firmus* (II-20), *Bacillus firmus* I-1582 (BioNem, Votivo) (II-20a), *Metarhizium* (II-21), Mycorrhiza (II-22), *Hirsutella* (II-23), 4-{[(6-bromopyrid-3-yl)methyl](2-fluoroethyl) amino}furan-2(5H)-one (II-24), 4-{[(6-fluoropyrid-3-yl)methyl](2,2-difluoroethyl)amino}furan-2(5H)-one (II-25), 4-{[(2-chloro-1,3-thiazol-5-yl)methyl](2-fluoroethyl) amino}furan-2(5H)-one (II-26), 4-{[(6-chloropyrid-3-yl) methyl](2-fluoroethyl)amino}furan-2(5H)-one (II-27), 4-{[(6-chloropyrid-3-yl)methyl](2,2-difluoroethyl) amino}furan-2(5H)-one (II-28), 4-{[(6-chloro-5-fluoropyrid-3-yl)-methyl](methyl)amino}furan-2(5H)-one (II-29), 4-{[(5,6-dichloropyrid-3-yl)methyl](2-fluoroethyl) amino}furan-2(5H)-one (II-30), 4-{[(6-chloro-5-fluoropyrid-3-yl)methyl] (cyclo-propyl)amino}furan-2(5H)-one (II-31), 4-{[(6-chloropyrid-3-yl)methyl](cyclopropyl) amino}furan-2(5H)-one (II-32), 4-{[(6-chloropyrid-3-yl) methyl](methyl)amino}furan-2(5H)-one (II-33), chlorantraniliprole (II-37) and sulfoxaflor (II-39).

Surprisingly, the fungicidal, insecticidal and/or acaricidal and/or nematicidal action, especially the nematicidal action, of the inventive active ingredient combinations, especially after soil application, is significantly higher than the sum of the actions of the individual active ingredients. There is an unforeseeable true synergistic effect, and not just additive actions.

Preference is given to active ingredient combinations comprising the compounds of the formula (I-1) and at least one active ingredient of the formula (II).

The following combinations are of particular interest:
(I-1)+(II-1), (I-1)+(II-2), (I-1)+(II-3), (I-1)+(II-4), (I-1)+(II-5), (I-1)+(II-6), (I-1)+(II-7), (I-1)+(II-8), (I-1)+(II-9), (I-1)+(II-10), (I-1)+(II-11), (I-1)+(I-1)+(II-13), (I-1)+(II-14), (I-1)+(II-15), (I-1)+(II-16), (I-1)+(II-17), (I-1)+(II-18), (I-1)+(II-19), (I-1)+(II-20), (I-1)+(II-20a), (I-1)+(II-21), (I-1)+(II-22), (I-1)+(II-23), (I-1)+(II-24), (I-1)+(II-25), (I-1)+(II-26), (I-1)+(II-27), (I-1)+(II-28), (I-1)+(II-29), (I-1)+(II-30), (I-1)+(II-31), (I-1)+(II-32), (I-1)+(II-33), (I-1)+(II-34), (I-1)+(II-35), (I-1)+(II-36), (I-1)+(II-37), (I-1)+(II-38), (I-1)+(II-39), (I-1)+(II-40), (I-1)+(II-41), (I-1)+(II-42) and (I-1)+(II-43).

The active ingredient combinations may additionally also comprise further fungicidally, acaricidally or insecticidally active additive components.

When the active ingredients in the inventive active ingredient combinations are present in particular weight ratios, the improved action is particularly clearly evident. However, the weight ratios of the active ingredients in the active ingredient combinations can be varied within a relatively wide range. In general, the inventive combinations comprise active ingredients of the formula (I-1) and the mixing partner in the preferred and particularly preferred mixing ratios specified in the table below:

| Mixing partner | Preferred mixing ratio of (I-1):mixing partner | Particularly preferred mixing ratio of (I-1):mixing partner |
| --- | --- | --- |
| II-1 | 125:1 to 1:125 | 25:1 to 1:25 |
| II-2 | 125:1 to 1:125 | 25:1 to 1:25 |
| II-3 | 125:1 to 1:125 | 25:1 to 1:25 |
| II-4 | 125:1 to 1:125 | 25:1 to 1:25 |
| II-5 | 125:1 to 1:125 | 25:1 to 1:25 |
| II-6 | 125:1 to 1:125 | 25:1 to 1:25 |
| II-7 | 125:1 to 1:125 | 25:1 to 1:25 |
| II-8 | 125:1 to 1:125 | 25:1 to 1:25 |
| II-9 | 125:1 to 1:125 | 25:1 to 1:25 |
| II-10 | 125:1 to 1:125 | 25:1 to 1:25 |
| II-11 | 125:1 to 1:125 | 25:1 to 1:25 |
| II-12 | 125:1 to 1:125 | 25:1 to 1:25 |
| II-13 | 125:1 to 1:125 | 25:1 to 1:25 |
| II-14 | 200:1 to 1:200 | 50:1 to 1:50 |
| II-15 | 125:1 to 1:125 | 25:1 to 1:25 |
| II-16 | 125:1 to 1:125 | 25:1 to 1:25 |
| II-17 | 125:1 to 1:125 | 25:1 to 1:25 |
| II-18 | 125:1 to 1:125 | 25:1 to 1:25 |
| II-19 | 125:1 to 1:125 | 25:1 to 1:25 |
| II-20 | 125:1 to 1:125 | 25:1 to 1:25 |
| II-20-a | 125:1 to 1:125 | 25:1 to 1:25 |
| II-21 | 125:1 to 1:125 | 25:1 to 1:25 |
| II-22 | 125:1 to 1:125 | 25:1 to 1:25 |
| II-22 | 125:1 to 1:125 | 25:1 to 1:25 |
| II-23 | 125:1 to 1:125 | 25:1 to 1:25 |
| II-24 | 125:1 to 1:125 | 25:1 to 1:25 |
| II-25 | 125:1 to 1:125 | 25:1 to 1:25 |
| II-26 | 125:1 to 1:125 | 25:1 to 1:25 |
| II-27 | 125:1 to 1:125 | 25:1 to 1:25 |
| II-28 | 125:1 to 1:125 | 25:1 to 1:25 |
| II-29 | 125:1 to 1:125 | 25:1 to 1:25 |
| II-30 | 125:1 to 1:125 | 25:1 to 1:25 |
| II-31 | 125:1 to 1:125 | 25:1 to 1:25 |
| II-32 | 125:1 to 1:125 | 25:1 to 1:25 |
| II-33 | 125:1 to 1:125 | 25:1 to 1:25 |
| II-34 | 125:1 to 1:125 | 25:1 to 1:25 |
| II-35 | 125:1 to 1:125 | 25:1 to 1:25 |
| II-36 | 125:1 to 1:125 | 25:1 to 1:25 |
| II-37 | 125:1 to 1:125 | 25:1 to 1:25 |
| II-38 | 125:1 to 1:125 | 25:1 to 1:25 |
| II-39 | 125:1 to 1:125 | 25:1 to 1:25 |
| II-40 | 125:1 to 1:125 | 25:1 to 1:25 |
| II-41 | 125:1 to 1:125 | 25:1 to 1:25 |

-continued

| Mixing partner | Preferred mixing ratio of (I-1):mixing partner | Particularly preferred mixing ratio of (I-1):mixing partner |
| --- | --- | --- |
| II-42 | 125:1 to 1:125 | 25:1 to 1:25 |
| II-43 | 125:1 to 1:125 | 25:1 to 1:25 |

An alternative embodiment of the present invention relates to nematicidal active ingredient combinations comprising N-{2-[3-chloro-5-(trifluoromethyl)-2-pyridinyl]ethyl}-2-trifluoromethyl-benzamide (I-1) and at least one fungicidal active ingredient selected from the group consisting of benalaxyl, benalaxyl-M, bupirimate, clozylacon, dimethirimol, ethirimol, furalaxyl, hymexazol, metalaxyl, metalaxyl-M, ofurace, oxadixyl and oxolinic acid, benomyl, carbendazim, chlorfenazole, diethofencarb, ethaboxam, fuberidazole, pencycuron, thiabendazole, thiophanate, thiophanate-methyl and zoxamide, diflumetorim as inhibitor which acts on complex I of the respiratory chain; bixafen, boscalid, carboxin, fenfuram, flutolanil, fluopyram, furametpyr, furmecyclox, isopyrazam (9R component), isopyrazam (9S component), mepronil, oxycarboxin, penthiopyrad, thifluzamid as inhibitors which act on complex II of the respiratory chain; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as inhibitors which act on complex III of the respiratory chain, binapacryl, dinocap, fluazinam and meptyldinocap, fentin acetate, fentin chloride, fentin hydroxide and silthiofam, andoprim, blasticidin-S, cyprodinil, kasugamycin, kasugamycin hydrochloride hydrate, mepanipyrim and pyrimethanil, fenpiclonil, fludioxonil and quinoxyfen, biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole, benthiavalicarb, dimethomorph, flumorph, iprovalicarb, mandipropamid, polyoxins, polyoxorim, prothiocarb, validamycin A and valiphenal, carpropamid, diclocymet, fenoxanil, phthalide, pyroquilon and tricyclazole, acibenzolar-S-methyl, probenazole and tiadinil, Bordeaux mixture, captafol, captan, chlorothalonil, copper naphthenate, copper oxide, copper oxychloride, copper preparations such as, for example, copper hydroxide, copper sulphate, dichlofluanid, dithianon, dodine and its free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations such as, for example, calcium polysulphide, thiram, tolylfluanid, zineb and ziram, 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, N-{2-[1,1'-bi(cyclopropyl)-2-yl]phenyl}-3-(difluoromethyl)-1-methyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, O-{1-[4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-N²-(methylsulphonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiole, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulphonyl)pyridine, 2-butoxy-6-iodo-3-propyl-4H-chromen-4-one, 2-phenylphenol and salts thereof, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 8-hydroxyquinoline, 8-hydroxyquinoline sulphate, 5-methyl-6-octyl-3,7-dihydro[1,2,4]triazolo[1,5-a]pyrimidine-7-amine, 5-ethyl-6-octyl-3,7-dihydro[1,2,4]triazolo[1,5-a]pyrimidine-7-amine, benthiazol, bethoxazin, capsimycin, carvone, chinomethionat, chloroneb, cufraneb, cyflufenamide, cymoxanil, cyprosulfamide, dazomet, debacarb, dichlorophen, diclomezine, dicloran, difenzoquat, difenzoquat methylsulphate, diphenylamin, ecomat, ferimzone, flumetover, fluopicolide, fluoromide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3- chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts thereof, phenazine-1-carboxylic acid, phenothrin, phosphoric acid and salts thereof, propamocarb fosetylate, propanosine-sodium, proquinazid, pyrrolnitrin, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulphonohydrazide and zarilamide.

Animal Pests

Given good plant compatibility, the active ingredient combinations are suitable for controlling animal pests, such as insects and/or arachnids, especially nematodes, which are encountered in viticulture, fruit growing, in agriculture, in nurseries and in forests. They can preferably be used as crop protection agents. They are effective against normally sensitive and resistant species and against all or particular development stages. The abovementioned pests include:

Insects

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the *Dermaptera*, for example, *Forficula auricularia.*

From the order of the *Isoptera*, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

Arachnids

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

Nematodes

In principle, all kinds of plant-parasitic nematodes can be controlled with the inventive active ingredient combinations. The inventive active ingredient combinations are found to be particularly advantageous for controlling nematodes which are selected from the group consisting of: *Meloidogyne* spp., for example *Meloidogyne incognita, Meloidogyne javanica, Meloidogyne hapla, Meloidogyne arenaria; Ditylenchus* ssp., for example *Ditylenchus dipsaci, Ditylelenchus destructor; Pratylenchus* ssp., for example *Pratylenchus penetrans, Pratylenchus fallax, Pratylenchus coffeae, Pratylenchus loosi, Pratylenchus vulnus; Globodera* spp., for example *Globodera rostochiensis, Globodera pallida* etc.; *Heterodera* spp., such as *Heterodera glycines Heterodera shachtoii* etc.;

*Aphelenchoides* spp., for example *Aphelenchoides besseyi, Aphelenchoides ritzemabosi, Aphelenchoides fragarieae; Aphelenchus* ssp., for example *Aphelenchus avenae; Radopholus* ssp, for example *Radopholus similis; Tylenchulus* ssp., for example *Tylenchulus semipenetrans; Rotylenchulus* ssp., for example *Rotylenchulus reniformis;*

*Bursaphelenchus* spp., for example *Bursaphelenchus xylophilus, Aphelenchoides* spp., *Longidorus* spp., *Xiphinema* spp., *Trichodorus* spp.

In addition, the inventive active ingredient combinations are found to be effective for controlling nematodes which attack humans or animals, for example roundworm, pinworm, filaria, *Wuchereri bancrofti*, threadworms (convoluted filaria), *Gnathostoma* etc.

Animal Health

The inventive active ingredient combinations are effective not only against plant, hygiene and stored product pests, but also in the veterinary sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders *Amblycerina* and *Ischnocerina*, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders *Nematocerina* and *Brachycerina*, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredient combinations are also suitable for controlling arthropods which attack agricultural productive livestock, for example cattle, sheep, goats, horses, pigs, donkeys, camels, buffalo, rabbits, chickens, turkeys, ducks, geese and bees, other pets, for example dogs, cats, caged birds and aquarium fish, and also so-called test animals, for example hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the inventive active ingredient combinations.

The inventive active ingredient combinations are used in the veterinary sector and in animal husbandry in a known manner by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredient combinations can be used as formulations (for example powders, emulsions, flowables) comprising the active ingredients in an amount of 1 to 80% by weight, either directly or after 100 to 10 000-fold dilution, or they may be used as a chemical bath.

Crops

The crops to be protected, which have only been described in a general manner, are differentiated and specified below. Thus, with regard to use, vegetables are understood to mean, for example, fruit vegetables and flower-heads as vegetables, for example carrots, bell peppers, chilli peppers, tomatoes, aubergines, cucumbers, cucurbits, courgettes, broad beans, runner beans, bush beans, peas, artichokes, maize;

but also leafy vegetables, for example lettuce, chicory, endives, cress, rocket salad, field salad, iceberg lettuce, leek, spinach, swiss chard;

additionally tuber vegetables, root vegetables and stem vegetables, for example celeriac, beetroot, carrots, garden radish, horseradish, salsify, asparagus, table beet, palm shoots, bamboo shoots, and also bulb vegetables, for example onions, leek, fennel, garlic;

additionally brassica vegetables, such as cauliflower, broccoli, kohlrabi, red cabbage, white cabbage, green cabbage, savoy cabbage, brussels sprouts, chinese cabbage.

With regard to use, perennial crops are understood to mean citrus fruit, for example oranges, grapefruit, mandarins, lemons, limes, bitter oranges, kumquats, satsumas;

but also pome fruit, for example apples, pears and quince, and stone fruit, for example peaches, nectarines, cherries, plums, common plums, apricots;

additionally grapevine, hops, olives, tea, soya, rape, cotton, sugar cane, beet, potatoes, tobacco and tropical crops, for example mangoes, papayas, figs, pineapples, dates, bananas, durians, kakis, coconuts, cacao, coffee, avocados, lychees, maracujas, guavas, and also almonds and nuts, for example hazelnuts, walnuts, pistachios, cashew nuts, brazil nuts, pecan nuts, butter nuts, chestnuts, hickory nuts, macadamia nuts, peanuts, and additionally also soft fruit, for example blackcurrants, gooseberries, raspberries, blackberries, blueberries, strawberries, red bilberries, kiwis, cranberries.

With regard to use, ornamental plants are understood to mean annual and perennial plants, for example cut flowers, for example roses, carnations, gerbera, lilies, marguerites, chrysanthemums, tulips, daffodils, anemones, poppies, amaryllis, dahlias, azaleas, malves, but also, for example, bedding plants, potted plants and shrubs, for example roses, tagetes, pansies, geraniums, fuchsias, hibiscus, chrysanthemums, busy lizzies, cyclamen, african violets, sunflowers, begonias, in ornamental lawns, in golf lawns, but also in cereals such as barley, wheat, rye, triticale, oats, in rice, in millet and sorghum, in maize, additionally, for example, bushes and conifers, for example fig trees, rhododendron, spruce trees, fir trees, pine trees, yew trees, juniper trees, stone pines, rose bays.

With regard to use, spices are understood to mean annual and perennial plants, for example aniseed, chilli pepper, bell pepper, pepper, vanilla, marjoram, thyme, cloves, juniper berries, cinnamon, tarragon, coriander, saffron, ginger.

According to the invention, it is possible to treat all plants and plant parts. Plants are understood here to mean all plants and plant populations such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which can and cannot be protected by plant breeders' certificates.

GMOs

In a further preferred embodiment, transgenic plants and plant cultivars which have been obtained by genetic engineering methods, if appropriate in combination with conventional methods (Genetically Modified Organisms), and parts thereof are treated. The terms "parts" and "plant parts" have been explained above.

More preferably, plants of the plant cultivars which are in each case commercially available or in use are treated in accordance with the invention.

Depending on the plant species or plant cultivars, their location and growth conditions (soils, climate, vegetation period, diet), the treatment in accordance with the invention may also result in superadditive ("synergistic") effects. For example, reduced application rates and/or a widening of the activity spectrum and/or an increase in the activity of the substances and compositions which can be used in accordance with the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processibility of the harvested products are possible which exceed the effects which were actually to be expected.

The transgenic plants or plant cultivars (i.e. those obtained by genetic engineering) which are preferred and to be treated in accordance with the invention include all plants which, through the genetic modification, received genetic material which imparts particular advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processibility of the harvested products. Further and particularly emphasized examples of such properties are a better defence of the plants against animal and microbial pests, such as against insects, mites, nematodes, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed in the plants by the genetic material from *Bacillus Thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active ingredients, for example imidazolinones, sulphonylureas, ACCases, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plant cultivars will be developed and/or marketed in the future.

The plants listed can be treated in accordance with the invention in a particularly advantageous manner with the inventive active ingredient mixture. The preferred ranges stated above for the mixtures also apply to the treatment of these plants. Particular emphasis is given to the treatment of plants with the mixture specifically mentioned in the present text.

The control of phytopathogenic fungi or animal pests, especially of nematodes, by treating the seed of plants has been known for a long time and is the subject of continuous improvements. However, in the treatment of seed, a number of problems are encountered which cannot always be resolved in a satisfactory manner. Thus, it is desirable to develop methods for protecting the seed and the germinating plant which significantly reduce, or make superfluous, the additional application of crop protection agents after sowing or after the emergence of the plants. It is additionally desirable to optimize the amount of active ingredient employed in such a way as to provide maximum protection for the seed and the germinating plant from attack by phytopathogenic fungi or animal pests, especially nematodes, but without damaging the plant itself by the active ingredient used. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates especially to a method for the protection of seed and germinating plants from attack by phytopathogenic fungi or animal pests, especially by nematodes, by treating the seed with an inventive composition.

The invention likewise relates to the use of the inventive compositions for the treatment of seed for protecting the seed and the germinating plant from phytopathogenic fungi or animal pests, especially from nematodes.

The invention further relates to seed which has been treated with an inventive composition for protection from phytopathogenic fungi or animal pests, especially nematodes.

One of the advantages of the present invention is that the particular systemic properties of the inventive compositions mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the inventive mixtures can also be used for transgenic seed in particular.

Formulations

The active ingredient combinations can be converted to the customary formulations such as solutions, emulsions, wettable powders, suspensions, powders, dusts, pastes, soluble powders, granules, suspension-emulsion concentrates, natural and synthetic materials impregnated with active ingredient, and microencapsulations in polymeric materials for the foliar and soil applications.

These formulations are produced in a known manner, for example by mixing the active ingredients with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Useful solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use dyes such as inorganic pigments, for example iron oxide, titanium oxide and Prussian Blue, and organic colorants such as alizarin dyes, azo dyes and metal phthalocyanine dyes, and trace nutrients such as salts of iron, manganese, boron, copper, cobalt, molybdenum and zinc.

The formulations generally contain between 0.1 and 95% by weight of active ingredient, preferably between 0.5 and 90%.

The inventive active ingredient combinations may be present in commercially standard formulations and in the use forms, prepared from these formulations, as a mixture with other active ingredients, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixing with other known active ingredients such as herbicides or with fertilizers and growth regulators is also possible.

When used as insecticides, the inventive active ingredient combinations may additionally be present in their commercially available formulations and in the use forms, prepared from these formulations, as a mixture with synergists. Synergists are compounds which enhance the action of the active ingredients, without it being necessary for the synergist added to be active itself.

The active ingredient content of the use forms prepared from the commercially available formulations may vary within wide limits. The active ingredient concentration of the use forms may be from 0.0000001 to 95% by weight of active ingredient, preferably between 0.0001 and 50% by weight.

The compounds are employed in a customary manner appropriate for the use forms.

Use Forms

Foliar Applications

Foliar application is understood to mean the inventive treatment of the plants and plant parts with the active ingredients directly or by action on the environment, habitat or storage space thereof by the customary treatment methods, for example by dipping, spraying, vaporizing, nebulizing, scattering, painting and injecting. Plant parts are understood to mean all above-ground and below-ground parts and organs of plants, such as shoot, leaf, flower and root, examples including leaves, needles, stems, stalks, flowers, fruit-bodies, fruits and seeds, and also roots, tubers and rhizomes. The plant parts also include harvested plants and vegetative and generative propagation material, for example seedlings, tubers, rhizomes, cuttings and seeds.

Soil Application

Soil application is understood to mean the control of insects and/or spider mites and/or nematodes by drenching pesticides onto the soil, incorporating them into the soil and in irrigation systems as droplet application onto the soil. Alternatively, the inventive active ingredient combinations can be introduced into the site of the plants in solid form (for example in the form of granules). In the case of paddy rice crops, this may also be accomplished by metering the inventive active ingredient combinations in a solid application form (for example as a granule) into a flooded paddy field.

The invention relates to these application forms to natural (soil) or artificial substrates (for example rock wool, glass wool, quartz sand, pebbles, expanded clay, vermiculite), outdoors or in closed systems (e.g. greenhouses or under film cover) and in annual (e.g. vegetables, potatoes, cotton, beet, ornamental plants) or perennial crops (e.g. citrus plants, fruit, tropical crops, spices, nuts, vines, conifers and ornamental plants). It is additionally possible to deploy the active ingredients by the ultra-low-volume method or to inject the active ingredient formulation or the active ingredient itself into the soil.

Seed Treatment

The inventive active ingredient combinations are suitable especially for protection of seed of any plant variety which is used in agriculture, in greenhouses, in forests or in gardening from the aforementioned animal pests, especially from nematodes. More particularly, the seed is that of cereals (such as wheat, barley, rye, millet and sorghum, and oats), maize, cotton, soya, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of cereals (such as wheat, barley, rye and oats), maize and rice, and the treatment of cotton and soya seed.

In the context of the present invention, the inventive composition is applied on its own or in a suitable formulation to the seed. Preferably, the seed is treated in a state in which it is sufficiently stable that the treatment does not cause any damage. In general, treatment of the seed may take place at any point in time between harvesting and sowing. Typically, the seed used has been separated from the plant and freed from cobs, shells, stalks, coats, hairs or the flesh of the fruits. For example, it is possible to use seed which has been harvested, cleaned and dried to a moisture content of less than 15% by weight. Alternatively, it is also possible to use seed which, after drying, has been treated, for example, with water and then dried again.

When treating the seed, it generally has to be ensured that the amount of the inventive composition applied to the seed and/or the amount of further additives is selected such that the germination of the seed is not adversely affected, and that the resulting plant is not damaged. This must be borne in mind in particular in the case of active ingredients which may exhibit phytotoxic effects at certain application rates.

The inventive active ingredient combinations/compositions can be applied directly, i.e. without comprising any further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876, 739 A, US 2003/0176428 A1, WO 2002/080675 A1, WO 2002/028186 A2.

The active ingredient combinations usable in accordance with the invention can be converted to the customary seed dressing product formulations such as solutions, emulsions, suspensions, powders, foams, slurries and other coating compositions for seed, and ULV formulations.

These formulations are prepared in the known manner by mixing the active ingredients or active ingredient combinations with customary additives, for example customary extenders and also solvents or diluents, dyes, wetters, dispersants, emulsifiers, antifoams, preservatives, secondary thickeners, adhesives, gibberellins, and also water.

The dyes which may be present in the seed dressing product formulations usable in accordance with the invention are all dyes which are customary for such purposes. Both pigments, which are sparingly soluble in water, and dyes, which are soluble in water, may be used. Examples of dyes include those known by the names Rhodamine B, C.I. Pigment Red 112 and C.I. Solvent Red 1.

The wetters which may be present in the seed dressing product formulations usable in accordance with the invention are all substances which are conventionally used for the formulation of active agrochemical ingredients and for promoting wetting. Alkylnaphthalenesulphonates, such as diisopropyl- or diisobutylnaphthalenesulphonates, can be used with preference.

Useful dispersants and/or emulsifiers which may be present in the seed dressing product formulations usable in accordance with the invention are all nonionic, anionic and cationic dispersants which are conventionally used for the formulation of active agrochemical ingredients. Nonionic or anionic dispersants or mixtures of nonionic or anionic dispersants can be used with preference. Suitable nonionic dispersants include, in particular, ethylene oxide/propylene oxide block polymers, alkylphenol polyglycol ethers and tristyrylphenol polyglycol ethers, and their phosphated or sulphated derivatives. Suitable anionic dispersants are, in particular, lignosulphonates, polyacrylic acid salts and arylsulphonate/formaldehyde condensates.

The antifoams which may be present in the seed dressing product formulations usable in accordance with the invention are all foam-suppressing substances conventionally used for the formulation of active agrochemical ingredients. Silicone antifoams and magnesium stearate can be used with preference.

The preservatives which may be present in the seed dressing product formulations usable in accordance with the invention are all substances which can be employed in agrochemical compositions for such purposes. Examples include dichlorophene and benzyl alcohol hemiformal.

The secondary thickeners which may be present in the seed dressing product formulations usable in accordance with the invention are all substances which can be employed in agrochemical compositions for such purposes. Cellulose derivatives, acrylic acid derivatives, xanthan, modified clays and finely divided silica are preferred.

The adhesives which may be present in the seed dressing product formulations usable in accordance with the invention are all customary binders which can be employed in seed dressing products. Preference is given to polyvinylpyrrolidone, polyvinyl acetate, polyvinyl alcohol and tylose.

The gibberellins which may be present in the seed dressing product formulations usable in accordance with the invention are preferably the gibberellins A1, A3 (=gibberellic acid), A4 and A7, particular preference being given to using gibberellic acid. The gibberellins are known (cf. R. Wegler "Chemie der Pflanzenschutz- and Schädlingsbekämpfungsmittel" [Chemistry of Plant Protectants and Pesticides], Vol. 2, Springer Verlag, 1970, pp. 401-412).

The seed dressing product formulations usable in accordance with the invention can be employed either directly or after preceding dilution with water for the treatment of a wide range of seeds. For instance, the concentrates or the formulations obtainable therefrom by dilution with water can be used to dress the seed of cereals, such as wheat, barley, rye, oats and triticale, and the seed of maize, rice, rape, peas, beans, cotton, soya, sunflowers and beet, or else a wide variety of different vegetable seeds. The seed dressing product formulations usable in accordance with the invention or the dilute preparations thereof can also be used to dress seed of transgenic plants. In this context, additional synergistic effects may also occur as a consequence of the interaction with the substances formed by expression.

Useful apparatus which can be used to treat seed with the seed dressing product formulations usable in accordance with the invention, or with the preparations prepared therefrom by addition of water, is all mixing apparatus which can typically be used to dress seed. Specifically, the seed dressing procedure is to place the seed into a mixer, add the amount of seed dressing product formulation desired in each case, either as such or after preceding dilution with water, and mix the contents of the mixer until the formulation has been distributed homogeneously on the seed. If appropriate, this is followed by a drying process.

The application rate of the seed dressing product formulations usable in accordance with the invention can be varied within a relatively wide range. It is guided by the particular content of the active ingredients in the formulations and by the seed. The application rates of the active ingredient combinations are generally between 0.001 and 50 g per kilogram of seed, preferably between 0.01 and 25 g per kilogram of seed.

BIOLOGICAL EXAMPLES

The expected efficacy of a given combination of two compounds is calculated as follows (see Colby, S. R., "Calculating Synergistic and antagonistic Responses of Herbicide Combinations", Weeds 15, pp. 20-22, 1967):

If

X is the efficacy expressed in % mortality of the untreated control for test compound A at a concentration of m ppm respectively m g/ha, Y is the efficacy expressed in % mortality of the untreated control for test compound B at a concentration of n ppm respectively n g/ha, E is the efficacy expressed in % mortality of the untreated control using the mixture of A and B at m and n ppm respectively m and n g/ha, then is $$E = X + Y \frac{X \cdot Y}{100}$$

If the observed insecticidal efficacy of the combination is higher than the one calculated as "E", then the combination of the two compounds is more than additive, i.e., there is a synergistic effect.

Example A

*Meloidogyne incognita*—Test (MELGIN)

| Solvent: | 7 parts by weight of dimethylformamide |
|---|---|
| Emulsifier: | 1 parts by weight of alkylarylpolyglycolether |

To produce a suitable preparation of active compound, 1 part by weight of active compound is mixed with the stated amount of solvent, and the concentrate is diluted with emulsifier-containing water to the desired concentration.

Vessels are filled with sand, a solution of the active ingredient, a suspension containing eggs and larvae of *Meloidogyne incognita* and salad seeds. The salad seeds germinate and the seedlings grow. Galls develop on the roots.

After the specified period the nematicidal activity is determined on the basis of the percentage of gall formation. 100% means that no galls were found; 0% means that the number of galls found on the roots of the treated plants was equal to that in untreated control plants.

In this test for example, the following combination shows a superior effect compared to the single compounds.

TABLE 1

| Meloidogyne incognita - Test | | | |
|---|---|---|---|
| Active Ingredient | Concentration in ppm | Mortality in % after $21^d$ | |
| Fluopyram | 0.125 | 56 | |
| Cyazypyr | 4 | 6 | |
| | | obs.* | cal.** |
| Fluopyram + Cyazypyr According to the invention | 0.125 + 4 | 68 | 58.64 |

*obs. = observed insecticidal efficacy
**cal. = efficacy calculated with Colby-formula

The invention claimed is:

1. A nematicidal active ingredient composition comprising a synergistically effective amount of:
   (I) N-{2-[3-chloro-5-(trifluoromethyl)-2-pyridinyl]ethyl}-2-trifluoromethyl-benzamide (I-1) or an N-oxide thereof; and
   (II) at least one insecticidal or nematicidal active ingredient selected from the group consisting of *Bacillus firmus*, *Metarhizium*, 4-{[(6-chloropyrid-3-yl)methyl](2,2-difluoroethyl)amino}furan-2(5H)-one, cyazypyr, and 5-chloro-2-[(3,4,4-trifluorobut-3-en-1-yl)sulphonyl]-1,3-thiazole.

2. The composition according to claim 1 wherein the insecticidal or nematicidal active ingredient (II) is selected from the group consisting of *Bacillus firmus*, *Metarhizium*, and 4-{[(6-chloropyrid-3-yl)methyl](2,2-difluoroethyl)amino}furan-2(5H)-one.

3. A method for controlling animal pests, comprising allowing the composition as defined in claim 1 to act on the leaves, flowers, stem or the seed of the plants to be protected, on animal pests, the habitat thereof, the soil, or combinations thereof.

4. A process for producing insecticidal, acaricidal, nematicidal compositions, or combinations thereof, comprising mixing the composition as defined in claim 1 with one or more extenders, surfactants, or combinations thereof.

5. Seed comprising the composition as defined in claim 1.

6. A method for controlling animal pests, comprising allowing the composition as defined in claim 1 to act on seed.

7. A method for controlling animal pests, comprising allowing the composition as defined in claim 1 to act on soil or artificial substrates.

8. A method according to claim 3, wherein the animal pests are nematodes.

9. The method of claim 8, wherein said at least one insecticidal or nematicidal active ingredient (II) is cyazypyr.

10. The method of claim 9, wherein the weight ratio of the compound I-1 to cyazypyr is from 125:1 to 1:125.

11. The method of claim 10, wherein the weight ratio of the compound I-1 to cyazypyr is from 25:1 to 1:25.

12. The method of claim 10, wherein the weight ratio of the compound I-1 to cyazypyr is 1:32.

13. The composition of claim 1, wherein said at least one insecticidal or nematicidal active ingredient (II) is cyazypyr.

14. The composition of claim 13, wherein the weight ratio of the compound I-1 to cyazypyr is from 125:1 to 1:125.

15. The composition of claim 14, wherein the weight ratio of the compound I-1 to cyazypyr is from 25:1 to 1:25.

16. The composition of claim 15, wherein the weight ratio of the compound I-1 to cyazypyr is 1:32.

17. The composition of claim 1, wherein said at least one insecticidal or nematicidal active ingredient (II) is *Bacillus firmus*.

18. The composition of claim 1, wherein said at least one insecticidal or nematicidal active ingredient (II) is 4-{[(6-chloropyrid-3-yl)methyl](2,2-difluoroethyl)amino}furan-2(5H)-one.

19. The composition of claim 1, wherein said at least one insecticidal or nematicidal active ingredient (II) is 5-chloro-2-[(3,4,4-trifluorobut-3-en-1-yl)sulphonyl]-1,3-thiazole.

20. The composition of claim 1, wherein said at least one insecticidal or nematicidal active ingredient (II) is *Metarhizium*.

21. The composition of claim 17, wherein the weight ratio of the compound I-1 to *Bacillus firmus* is from 125:1 to 1:125.

22. The composition of claim 17, wherein the weight ratio of the compound I-1 to *Bacillus firmus* is from 25:1 to 1:25.

23. The composition of claim 18, wherein the weight ratio of the compound I-1 to 4-{[(6-chloropyrid-3-yl)methyl](2,2-difluoroethyl)amino}furan-2(5H)-one is from 125:1 to 1:125.

24. The composition of claim 18, wherein the weight ratio of the compound I-1 to 4-{[(6-chloropyrid-3-yl)methyl](2,2-difluoroethyl)amino}furan-2(5H)-one is from 25:1 to 1:25.

25. The composition of claim 19, wherein the weight ratio of the compound I-1 to 5-chloro-2-[(3,4,4-trifluorobut-3-en-1-yl)sulphonyl]-1,3-thiazole is from 125:1 to 1:125.

26. The composition of claim 19, wherein the weight ratio of the compound I-1 to 5-chloro-2-[(3,4,4-trifluorobut-3-en-1-yl)sulphonyl]-1,3-thiazole is from 25:1 to 1:25.

27. The composition of claim 20, wherein the weight ratio of the compound I-1 to *Metarhizium* is from 125:1 to 1:125.

28. The composition of claim 20, wherein the weight ratio of the compound I-1 to *Metarhizium* is from 25:1 to 1:25.

* * * * *